US011302417B2

(12) United States Patent
Gao et al.

(10) Patent No.: US 11,302,417 B2
(45) Date of Patent: Apr. 12, 2022

(54) SYSTEMS AND METHODS FOR SNP CHARACTERIZATION AND IDENTIFYING OFF TARGET VARIANTS

(71) Applicant: Affymetrix, Inc., Carlsbad, CA (US)

(72) Inventors: Hong Gao, Santa Clara, CA (US); Ali Pirani, Santa Clara, CA (US); Teresa Webster, Santa Clara, CA (US); Mei-Mei Shen, Santa Clara, CA (US)

(73) Assignee: Affymetrix, Inc., Carlsbad, CA (US)

( * ) Notice: Subject to any disclaimer, the term of this patent is extended or adjusted under 35 U.S.C. 154(b) by 577 days.

(21) Appl. No.: 16/197,267

(22) Filed: Nov. 20, 2018

(65) Prior Publication Data
US 2019/0198134 A1 Jun. 27, 2019

Related U.S. Application Data

(62) Division of application No. 13/844,285, filed on Mar. 15, 2013, now abandoned.

(51) Int. Cl.
G01N 33/48 (2006.01)
G16B 20/20 (2019.01)
G16B 20/00 (2019.01)

(52) U.S. Cl.
CPC ............ G16B 20/20 (2019.02); G16B 20/00 (2019.02)

(58) Field of Classification Search
None
See application file for complete search history.

(56) References Cited

U.S. PATENT DOCUMENTS

| | | | |
|---|---|---|---|
| 5,143,854 A | 9/1992 | Pirrung et al. | |
| 5,436,327 A | 7/1995 | Southern et al. | |
| 5,474,796 A | 12/1995 | Brennan | |
| 5,545,531 A | 8/1996 | Rava et al. | |
| 5,658,802 A | 8/1997 | Hayes et al. | |
| 5,744,305 A | 4/1998 | Fodor et al. | |
| 5,770,151 A | 6/1998 | Roach et al. | |
| 5,807,522 A | 9/1998 | Brown et al. | |
| 5,945,334 A | 8/1999 | Besemer et al. | |
| 5,981,733 A | 11/1999 | Gamble et al. | |
| 6,101,946 A | 8/2000 | Martinsky | |
| 6,140,044 A | 10/2000 | Besemer et al. | |
| 6,223,127 B1 | 4/2001 | Berno | |
| 6,242,266 B1 | 6/2001 | Schleifer et al. | |
| 6,300,063 B1 | 10/2001 | Lipshutz et al. | |
| 6,355,431 B1 | 3/2002 | Chee et al. | |
| 6,375,903 B1 | 4/2002 | Cerrina et al. | |
| 6,429,027 B1 | 8/2002 | Chee et al. | |
| 6,660,233 B1 | 12/2003 | Coassin et al. | |
| 6,687,692 B1 | 2/2004 | Balaban et al. | |
| 6,850,846 B2 | 2/2005 | Wang et al. | |
| 6,988,040 B2 | 1/2006 | Mei et al. | |
| 7,031,846 B2 | 4/2006 | Kaushikkar et al. | |
| 7,099,777 B1 | 8/2006 | Ghandour | |
| 7,332,273 B2 | 2/2008 | Trulson et al. | |
| 7,510,841 B2 | 3/2009 | Stuelpnagel et al. | |
| 7,745,091 B2 | 6/2010 | True | |
| 7,745,092 B2 | 6/2010 | True | |
| 8,200,440 B2 | 6/2012 | Hubbell et al. | |
| 2002/0168651 A1 | 11/2002 | Cawley et al. | |
| 2003/0120431 A1 | 6/2003 | Williams et al. | |
| 2004/0038388 A1 | 2/2004 | Yamamoto et al. | |
| 2004/0117128 A1 | 6/2004 | Cheng | |
| 2004/0157243 A1 | 8/2004 | Huang et al. | |
| 2005/0009069 A1 | 1/2005 | Liu et al. | |
| 2005/0023672 A1 | 2/2005 | Oostman et al. | |
| 2005/0123971 A1 | 6/2005 | Di et al. | |
| 2006/0088863 A1 | 4/2006 | Yamamoto et al. | |
| 2006/0134674 A1 | 6/2006 | Huang et al. | |
| 2006/0234371 A1 | 10/2006 | Shirazi | |
| 2006/0246576 A1 | 11/2006 | Shirazi | |
| 2007/0128647 A1 | 6/2007 | Huang et al. | |
| 2008/0003667 A1 | 1/2008 | Jones et al. | |
| 2008/0213775 A1* | 9/2008 | Brody | C12Q 1/6883 435/6.11 |
| 2009/0149340 A1 | 6/2009 | True | |
| 2010/0227279 A1 | 9/2010 | True | |
| 2010/0227770 A1 | 9/2010 | True | |
| 2010/0248981 A1 | 9/2010 | Shirazi | |
| 2010/0297448 A1 | 11/2010 | True et al. | |
| 2011/0093209 A1* | 4/2011 | Jones | G16B 20/10 702/19 |
| 2011/0136699 A1 | 6/2011 | Shirazi | |
| 2011/0159608 A1* | 6/2011 | Graham | A61P 27/02 436/501 |
| 2011/0303027 A1 | 12/2011 | Shirazi et al. | |
| 2014/0274749 A1 | 9/2014 | Gao et al. | |

OTHER PUBLICATIONS

Fazayeli, Farideh, Lipo Wang, and Jacek Mandziuk. "Feature selection based on the rough set theory and expectation-maximization clustering algorithm." International Conference on Rough Sets and Current Trends in Computing. Springer, Berlin, Heidelberg, 2008.*
Do, Chuong B., and Serafim Batzoglou. "What is the expectation maximization algorithm?." Nature biotechnology 26.8 (2008): 897-899.*
Wan et al. "Hybridization modeling of oligonucleotide SNP arrays for accurate DNA copy number estimation" (Nucleic Acids Research, vol. 37 (2009) pp. 1-12).*
Yang et al., "A customized and versatile high-density genotyping array for the mouse," Nature Methods, vol. 6, No. 9, 2009, 10 pages.
"BRLMM-P: a Genotype Calling Method for the SNP 5.0 Array," AFFYMETRIX, Revision date: Feb. 13, 2007, 16 pages.
Didion et al., "Discovery of novel variants in genotyping arrays improves genotype retention and reduces ascertainment bias," BMC Genomics, vol. 13, No. 1, 2012, 18 pages.

(Continued)

Primary Examiner — Anna Skibinsky
(74) Attorney, Agent, or Firm — Mauriel Kapouytian Woods LLP; Andrew A. Noble; Michael Muriel

(57) ABSTRACT

Methods for processing data using information gained from examining biological materials identifies and characterized probes for Single Nucleotide Polymorphisms and identifies Off Target Variants.

17 Claims, 12 Drawing Sheets

(56) References Cited

OTHER PUBLICATIONS

Voorrips et al., "Genotype calling in tetraploid species from bi-allelic marker data using mixture models," BMC Bioinformatics, vol. 12, No. 1, 2011, 11 pages.

"Affymetrix White Paper: Quality Control Assessment in Genotyping Console," AFFYMETRIX, Sep. 30, 2008, 12 pages.

Yang et al., "Subspecific origin and haplotype diversity in the laboratory mouse," Nature Genetics, vol. 43, No. 7, 2011, 17 pages.

\* cited by examiner

Before OTV typing

After OTV typing

|     | probeset_id | CR       | FLD      | HomFLD   | HetSO      |
|-----|-------------|----------|----------|----------|------------|
| 2   | ps1         | 100.0000 | 9.531076 | 22.00515 | 0.4648224  |
| 11  | ps10        | 100.0000 | NA       | NA       | NA         |
| 101 | ps100       | 98.6622  | 10.178726| 20.97348 | 0.3436559  |
| 102 | ps101       | 100.0000 | 8.373248 | 18.73123 | 0.1021297  |
| 103 | ps102       | 99.3311  | 4.800623 | 10.00725 | 0.2294279  |

|     | HomRO   | nMinorAllele | Nclus | n_AA | n_AB | n_BB | n_NC |
|-----|---------|--------------|-------|------|------|------|------|
| 2   | 2.20977 | 53           | 3     | 249  | 47   | 3    | 0    |
| 11  | 1.14658 | 0            | 1     | 0    | 0    | 299  | 0    |
| 101 | 2.23452 | 224          | 3     | 118  | 130  | 47   | 4    |
| 102 | 1.80295 | 167          | 3     | 22   | 123  | 154  | 0    |
| 103 | 1.65375 | 175          | 3     | 151  | 117  | 29   | 2    |

|     | hemizygous |
|-----|------------|
| 2   | 0          |
| 11  | 0          |
| 101 | 0          |
| 102 | 0          |
| 103 | 0          |

*FIG. 9A*

|     | probeset_id | CR       | FLD      | HomFLD   | HetSO      |
|-----|-------------|----------|----------|----------|------------|
| 57  | snp1        | 97.7528  | 8.221134 | 18.16312 | -0.7530729 |
| 382 | snp10       | 98.8764  | 4.849083 | 11.40189 | -0.7421616 |
| 61  | snp100      | 100.0000 | 13.244055| 27.99686 | 0.3148804  |
| 62  | snp101      | 100.0000 | NA       | 15.81937 | NA         |
| 63  | snp102      | 100.0000 | 6.578124 | 13.47439 | 0.3334340  |

|     | HomRO     | nMinorAllele | Nclus | n_AA | n_AB | n_BB | n_NC |
|-----|-----------|--------------|-------|------|------|------|------|
| 57  | 1.35594   | 81           | 3     | 45   | 3    | 39   | 2    |
| 382 | 1.44359   | 62           | 3     | 54   | 6    | 28   | 1    |
| 61  | 1.48463   | 55           | 3     | 27   | 1    | 61   | 0    |
| 62  | -0.360748 | 4            | 2     | 2    | 0    | 87   | 0    |
| 63  | 0.504862  | 26           | 3     | 10   | 6    | 73   | 0    |

|     | hemizygous |
|-----|------------|
| 57  | 0          |
| 382 | 0          |
| 61  | 0          |
| 62  | 0          |
| 63  | 0          |

*FIG. 9B*

Contrast = Log2(A_signal/B_signal)
Size = [Log2(A_signal) + Log2(B_signal)]/2

SYSTEMS AND METHODS FOR SNP CHARACTERIZATION AND IDENTIFYING OFF TARGET VARIANTS

CROSS REFERENCE TO RELATED APPLICATIONS

This application is a divisional of U.S. application Ser. No. 13/844,285 filed on Mar. 15, 2013. All referenced documents and applications herein and all documents referenced therein are incorporated herein by reference for all purposes. This application may be related to other patent applications and issued patents assigned to the assignee indicated above. These applications and issued patents are incorporated herein by reference to the extent allowed under applicable law.

COPYRIGHT NOTICE

Pursuant to 37 C.F.R. 1.71(e), applicant notes that a portion of this disclosure contains material that is subject to and for which is claimed copyright protection (such as, but not limited to, source code listings, screen shots, user interfaces, or user instructions, or any other aspects of this submission for which copyright protection is or may be available in any jurisdiction). The copyright owner has no objection to the facsimile reproduction by anyone of the patent document or patent disclosure, as it appears in the Patent and Trademark Office patent file or records. All other rights are reserved, and all other reproduction, distribution, creation of derivative works based on the contents, public display, and public performance of the application or any part thereof are prohibited by applicable copyright law.

APPENDIX

This application is being filed electronically with a source code appendix that sets out selected source code portions from a copyrighted software program, owned by the assignee of this patent document, which manifests the invention according to specific embodiments. This appendix and all other papers filed herewith, including papers filed in any attached Information Disclosure Statement (IDS), are incorporated herein by reference. The appendix contains further examples and information related to various embodiments of the invention at various stages of development.

Permission is granted to make copies of the appendices solely in connection with the making of facsimile copies of this patent document in accordance with applicable law; all other rights are reserved, and all other reproduction, distribution, creation of derivative works based on the contents, public display, and public performance of the appendix or any part thereof are prohibited by the copyright laws.

BACKGROUND

1. Field of the Invention

The present invention relates to systems and methods for processing data using information gained from examining biological material. In particular, a preferred embodiment of the invention relates to analysis of processed image data from scanned biological probe arrays for determining genotype information via identification of polymorphisms, e.g., Single Nucleotide Polymorphisms (SNPs), insertion/deletion polymorphisms (indels), whole or partial chromosome deletions or duplications.

2. Related Art

Synthesized nucleic acid probe arrays, such as Affymetrix® arrays (Affymetrix, Inc., Santa Clara, Calif.) in the form of GeneChip® array cartridges, peg array strips, and Axiom® peg array plates, Illumina® BeadArray® arrays (Illumina, Inc., San Diego, Calif.), and Agilent® SurePrint® arrays (Agilent Technologies, Inc., Santa Clara, Calif.) and spotted probe arrays, have been used to generate unprecedented amounts of information about biological systems. A variety of techniques are known for the manufacture and use of nucleic acid probe arrays, such as the techniques disclosed within, e.g., U.S. Pat. No. 5,143,854 to Pirrung et al.; U.S. Pat. No. 5,744,305 to Fodor et al.; U.S. Pat. No. 7,332,273 to Trulson et al.; U.S. Pat. Nos. 5,945,334 and 6,140,044 to Besemer et al.; U.S. Pat. No. 5,545,531 to Rava et al.; U.S. Pat. No. 6,660,233 to Coassin et al.; U.S. Patent Application Publication Nos. 2004/0038388 and 2006/0088863 to Yamamoto et al.; U.S. Patent Application Publication No. 2005/0023672 to Oostman et al.; U.S. Patent Application Publication No. 2008/0003667 to Jones et al.; U.S. Patent Application Publication Nos. 2006/0246576, 2006/0234371, 2011/0136699 and 2010/0248981 to Shirazi; pending U.S. patent application Ser. No. 13/157,268, filed Jun. 9, 2011; U.S. Pat. No. 6,242,266 to Schleifer et al.; U.S. Pat. No. 6,375,903 to Cerrina et al.; U.S. Pat. No. 5,436,327 to Southern et al.; U.S. Pat. No. 5,474,796 to Brennan; U.S. Pat. No. 5,658,802 to Hayes et al.; U.S. Pat. No. 5,770,151 to Roach et al.; U.S. Pat. No. 5,807,522 to Brown et al.; U.S. Pat. No. 5,981,733 to Gamble et al.; U.S. Pat. No. 6,101,946 to Martinsky; U.S. Pat. Nos. 6,355,431 and 6,429,027 to Chee et al.; U.S. Pat. No. 7,510,841 to Stuelpnagel et al., U.S. Pat. Nos. 7,745,091 and 7,745,092 to True; U.S. Patent Application Publication No. 2010/0297448 to True et al.; and U.S. Patent Application Publication Nos. 2010/0227279, 2010/0227770 and 2009/0149340 to True, all of which are expressly incorporated herein by reference for all purposes. For example, the Genome-Wide Human SNP Array 6.0 from Affymetrix, Inc. is able to genotype more than 900,000 SNPs while Axiom® Genotyping Arrays from Affymetrix, Inc. are able to genotype from a customizable selection of between 1,500 and 2.6 million SNPs per array. Analysis of genotype data from such microarrays may lead to the development of new drugs, new varieties or strains of organisms, including plants, animals, bacteria, archaea and fungi, new diagnostic tools and treatments based upon genetic information (including information tailored to specific target populations) and the correlation of such information to diseases such cancer, and agrigenomic testing to maximize the economic value of plant and animal species such as bovine, buffalo, chicken, rice, lettuce and pepper.

Many methods and techniques for genotyping are known in the art. For example, see U.S. Pat. Nos. 6,300,063; 6,687,692; 6,223,127; 7,099,777; 6,850,846; 6,988,040; and 7,031,846, each of which is incorporated by reference in their entireties. See also U.S. Published Patent Application Publication Nos. 2002/0168651; 2003/0120431; 2005/0123971; 2004/0157243; 2006/0134674; 2004/0117128; 2004/0117127; 2005/0009069; and 2007/0128647, each of where is incorporated by reference in their entireties.

The discussion of any work, publications, sales, or activity anywhere in this submission, including in any documents submitted with this application, shall not be taken as an admission that any such work constitutes prior art. The discussion of any activity, work, or publication herein is not an admission that such activity, work, or publication existed or was known in any particular jurisdiction.

Other Features & Benefits

The invention and various specific aspects and embodiments will be better understood with reference to the following drawings and detailed descriptions. For purposes of clarity, this discussion refers to devices, methods, and concepts in terms of specific examples. However, the invention and aspects thereof may have applications to a variety of types of devices and systems. It is therefore intended that the invention not be limited except as provided in the attached claims and equivalents.

Furthermore, it is well known in the art that logic systems and methods such as described herein can include a variety of different components and different functions in a modular fashion. Different embodiments of the invention can include different mixtures of elements and functions and may group various functions as parts of various elements. For purposes of clarity, the invention is described in terms of systems that include many different innovative components and innovative combinations of innovative components and known components. No inference should be taken to limit the invention to combinations containing all of the innovative components listed in any illustrative embodiment in this specification.

Before describing the present invention in detail, it is to be understood that this invention is not limited to particular compositions or systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content and context clearly dictates otherwise. Thus, for example, reference to "a device" includes a combination of two or more such devices, and the like.

Unless defined otherwise, technical and scientific terms used herein have meanings as commonly understood by one of ordinary skill in the art to which the invention pertains. Although any methods and materials similar or equivalent to those described herein can be used in practice or for testing of the present invention, the preferred materials and methods are described herein.

SUMMARY OF THE INVENTION

According to specific embodiments, the present invention is involved with methods and/or systems and/or devices that can be used together or independently to evaluate biological assay or testing or experiments and provide or evaluate results. In specific embodiments, the invention is involved with an information processing device, such as a computer or laboratory equipment, configured with logic instructions or modules to access data and perform steps as described herein. In further embodiments, the invention is involved with logic instructions and/or data recorded on a tangible media.

In SNP genotyping and other polymorphism genotyping, a no-call or incorrect genotype call can occur as the result of abnormal hybridization intensity for a sample at a given location. One source of genotype calling errors in this context is biological in origin and can be attributed to previously uncharacterized variation in genomic DNA, either in the sequence targeted by a probe set or with respect to the proximal and/or distal restriction sites used with certain reduced complexity genome-wide amplification approaches. These variants can reduce hybridization intensity sufficiently to eliminate or reverse the contrast between allelic probes such that an incorrect genotype call (or no-call) is made. These variants and are referred to herein as "off-target variants" (OTVs).

OTVs tend to produce an additional genotype cluster besides the normal two or three genotypes for diploid species: AA, AB and BB, or AA, BB. This cluster can be referred to as the variant or "V" cluster or OTV clusters. The OTV samples create problems in genotype calling. These samples are often miscalled as "AB," the heterozygote cluster. According to specific embodiments, systems and methods as described herein separate this OTV cluster from the other genotype clusters, thereby improving genotyping calls.

For example, the technique from MouseDivGenoR (Didion) package fails to detect some OTVs. The method uses an OTV score, a product of two p values for a sample to determine OTVs. The two p values measure deviation from the center of its cluster and deviation from the center of all the samples in terms of size dimension, respectively. Then the Didion method uses a nearest neighbor algorithm to cluster. The technique uses a stringent threshold (score>0.9999) and fails particularly when three genotype clusters exist, AA, BB, and V.

According to specific embodiments, an OTV genotype analysis uses the posterior information from a genotype cluster analysis (e.g., from an initial cluster algorithm, such as AxiomGT1) to initiate an expectation maximization (EM) algorithm or similar technique to determine whether an OTV cluster is present and identify which samples are in the OTV cluster. The method can also repeat the calls for samples in the AA, AB, and BB clusters. In particular embodiments, a post-processing technique for OTV-Typing uses a 2D EM algorithm with constraints to cluster based on both contrast and strength dimensions, where use of the strength dimension, according to specific embodiments, in determining OTV clusters is more extensive than use of the strength in the initial clustering In one example, the method uses clustering posteriors from the Affymetrix Power Tool AxiomGT1 algorithm as the starting points for AA, AB, BB and OTV clusters in the EM algorithm. Then the algorithm iteratively updates sample assignments and cluster centers until convergence.

According to further embodiments, an OTV genotype analysis is done as part of the overall genotype cluster analysis, using methods as described herein as will be understood to persons of skill in the art having benefit of the teachings provided herein.

In a number of prior methods and systems, part of the final genotyping analysis for at least some polymorphisms generally rested on a human expert or technician to either characterize one or more probesets according quality or select among multiple probesets for a particular polymorphisms based on perceived quality. In many genotyping devices or systems, there are more than one probes or probesets (e.g., 2 probes) for detecting a particular polymorphism. The probesets are in different locations on a gene chip, for example, but often adjacent to each other. Where 2 or more probesets existed for a polymorphism, a human technician viewing the data would select the probeset location for a particular polymorphism that "looked best" in terms of having strength, intensity, contrast, or shape characteristics that would be associated with a good set of genotyping calls. Where only one probeset exist for a polymorphism, a human technician viewing the data may characterized the results for a particular location as poor and possibly delete those results from the overall analysis.

According to further embodiments, SNP or other polymorphism data are analyzed by a computer system that determines a best probeset for one or more polymorphisms automatically so that a final best genotyping call can be made without expert human review. According to further embodiments, SNP or other polymorphism data are automatically classified by a computer system according to a number of quality classifications. In a specific embodiment, six example classifications are: (1) PolyHighResolution, characterized by good cluster resolution, and at least 2 example of the minor allele: (2) MonoHighResolution characterized by less than 2 examples of the minor allele usually due to low minor allele frequency (MAF) samples, but possible cluster fusion/compression; (3) OTV, where an OTV cluster has been called; (4) No Minor Hom characterized by two clusters with no examples of the minor homozygous genotypes; (5) Call Rate Below Threshold characterized by SNP call rate below threshold, but other cluster properties are above threshold; (6) Other, wherein one or more cluster properties are below threshold and therefore lower quality genotypes are likely.

According to further embodiments, a number of new quality metrics for SNP classification are defined.

BRIEF DESCRIPTION OF THE DRAWINGS

The above and further features will be more clearly appreciated from the following detailed description when taken in conjunction with the accompanying drawings. The file of this patent contains a least one drawing executed in color. Copies of this patent with color drawings will be provided by the United States Patent and Trademark Office upon request and payment of the necessary fee.

FIG. 9A illustrates an example output of a logic routine that determines genotyping data quality metrics or probeset assay data quality metrics according to specific embodiments.

FIG. 9B illustrates an example output of a logic routine that determines genotyping data quality metrics or probeset assay data quality metrics according to specific embodiments.

DESCRIPTION OF SPECIFIC EMBODIMENTS

Glossary

Figure 1A:
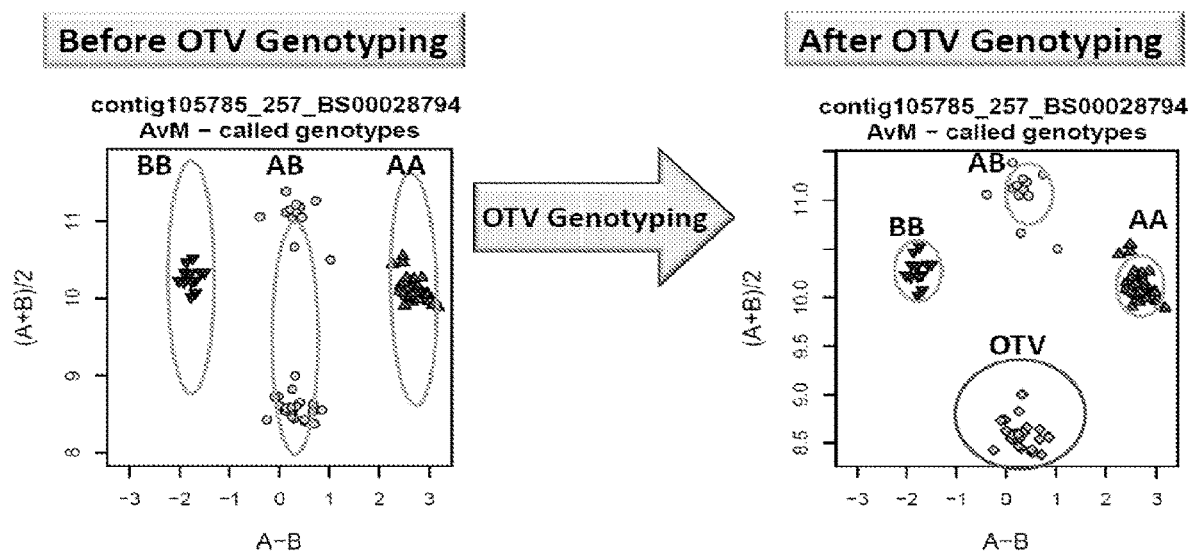
FIG. 1A provides examples of re-clustering or re-calling genotyping data after allowing for a variant cluster according to specific embodiments.

OTV stands for off target variant (OTV), which is a variant of a genomic DNA sequence that was previously uncharacterized or otherwise not accounted for within design of, e.g., a probe set intended to interrogate a SNP within that genomic DNA sequence. This unaccounted for variation in turn affects the overall intensity and contrast in the genotyping cluster data (e.g., the data associated with A and B allele signals) based upon the hybridization of the probes within the probe set with the OTV.

An OTV cluster is an additional genotype cluster that is utilized according to embodiments described herein to improve genotyping calls believed to be affected by OTVs. Thus, in the example of a diploid organism that presents three possible genotypes for a particular SNP (e.g., AA, BB, AB), an OTV cluster would be a fourth cluster used to improve the genotyping calls of AA, BB, and AB for the particular SNP within the samples at issue.

A single-nucleotide polymorphism (SNP, pronounced snip; plural snips) is a DNA sequence variation occurring when a single nucleotide—A, T, C or G—in the genome (or other shared sequence) differs between members of a biological species or paired chromosomes in a human. For example, two sequenced DNA fragments from different individuals, AAGCCTA to AAGCTTA, contain a difference in a single nucleotide. In this case, we say that there are two alleles. Almost all common SNPs have only two alleles. The genomic distribution of SNPs is not homogenous; SNPs usually occur in non-coding regions more frequently than in coding regions or, in general, where natural selection is acting and fixating the allele of the SNP that constitutes the most favorable genetic adaptation. Besides natural selection, other factors like genetic recombination and mutation rate can also determine SNP density. In many example species, one in 100-1000 nucleotides is a SNP. SNP frequency differs between ethnic/geographical groups. In some assay systems, methods used for distinguishing SNP alleles can also distinguish other alleles common in the genome, such as insertions/deletions. When used herein, unless the context requires, SNP encompasses any polymorphism that can be detected according to the methods for detecting SNPs.

Probesets are sets of oligonucleotide sequences that are used to determine the presence of a particular SNP.

Refs

1. Didion J P, Yang H, Sheppard K, Fu C P, McMillan L, Pardo-Manuel de Villena F, Churchill G A: Discovery of novel variants in genotyping arrays improves genotype retention and reduces ascertainment bias. BMC Genomics 2012, 13:34.

2. Yang H, Ding Y, Hutchins L N, Szatkiewicz J, Bell T A, Paigen B J, Graber J H, Pardo-Manuel de Villena F, Churchill G A: A customized and versatile high-density genotyping array for the mouse. Nat Methods 2009, 6:663-6.

3. Yang H, Wang J R, Didion J P, Buus R J, Bell T A, Welsh C E, Bonhomme F, Yu A H, Nachman M W, Pialek J, Tucker P, Boursot P, McMillan L, Churchill G A, Pardo-Manuel de Villena F: Subspecific origin and haplotype diversity in the laboratory mouse. Nat Genet. 2011 43:648-5.

OTVs

Overview

SNP analysis is a known tool for studying genetic variation generally in closely related subjects (e.g., different individuals of one species, different strains of a species, related or closely related species, etc.) Modern SNP genome analysis generally targets a very large number of SNPs and optionally some other polymorphisms, each having at least one probeset. In some systems, many polymorphisms may have two or more different probesets, with each of the different probesets providing a possible genotyping result for the polymorphism. In one method, an individual sample is exposed to a genotyping array or other probeset system to determine the presence of different polymorphism alleles in the sample. Because most organisms have multiple copies of every chromosome, there can be different alleles detected for the same sample. Thus, a sample is generally characterized by multiple alleles (e.g., 2) of each polymorphism. Determining the multiple alleles for a polymorphism is generally referred to in the art as genotyping or SNP genotyping.

One example of a recent, high-density, SNP detection array is the Affymetrix® Mouse Diversity Genotyping Array. The entire array is tiled (populated) with more than seven million 25-base pair oligonucleotide probes, which can assay nearly 625,000 SNPs and more than 900,000 invariant genomic probes (IGPs). The probes bind to labeled DNA from a target sample. Generally, analysis software is used to quantify the brightness of each fluorescing DNA-probe complex on a gridded image. High intensity spots indicate high affinity between the probe and target DNA sequences and are used to decode the genotypes of individual SNPs. Affymetrix provides other arrays, including human, dog, and other mouse arrays.

SNP or polymorphism genotype calling refers to the process of determining at a polymorphism location what alleles are present. In bi-allelic SNP polymorphisms, there are generally two different base pairs that can be present at a location, which may be referred to as allele A and allele B. The genotype of an SNP is generally one of (A, A), (B, B) or (A, B). The first two genotypes are generally referred to as homogeneous and the last as heterogeneous. The same is true for some other polymorphisms, such as a number of insertion/deletion polymorphisms.

Methods, comprising one or more of software programs, logic modules, and data capture systems, use a variety of methods to infer or determine discrete genotypes for an SNP location from continuous intensity data from a number of samples. Many methods, (such as the BRLMM-P or AxiomGT1 algorithm developed by Affymetrix) employ clustering of multiple samples based on the contrast between allelic probe intensities. Samples belonging to the two clusters with a large absolute contrast are called as homozygous genotypes and samples with low contrast are called as heterozygous genotypes. Samples that do not fall within any of the defined (e.g., two or three) clusters in the contrast dimension are generally uncalled, or null, often referred to as "no call." Aspects related to the BRLMM-P algorithm are discussed in U.S. Pat. No. 8,200,440 to Hubbell and assigned to Affymetrix. The entire contents of that patent, including all incorporated references, are incorporated herein by reference for all purposes. The BRLMM-P algorithm with some modifications and improvements is incorporated into the Affymetrix AxionGT1 analysis system.

A no-call or incorrect genotype call is the result of abnormal hybridization intensity for a sample at a given SNP location. One source of genotype calling errors is biological in origin and can be attributed to previously uncharacterized variation in genomic DNA, either in the sequence targeted by a probe set or in the proximal or distal restriction sites used for genome-wide amplification. These variants can reduce hybridization intensity sufficiently to eliminate or reverse the contrast between allelic probes such that an incorrect genotype call (or no-call) is made. Didion termed such variants "off-target variants" (OTVs) to distinguish them from the expected variant targeted by the SNP probe set and termed probe sets affected by OTVs as variable intensity oligonucleotides (VINOs) due to the dynamic effect of OTVs on hybridization intensity. In the present discussion, the term OTV is used to refer to the both the allele and probe sets affected by it. Genotyping errors due to uncharacterized sequence variation were largely unaddressed in prior SNP genotyping studies. Didion proposed a MouseDivGenoR genotype-calling algorithm implemented as a package for the R language that is claimed capable of recognizing OTVs and treating samples having OTVs as a distinct genotype class. Didion also proposed a tool for visualization of probe set hybridization intensities in which intensity contrast is plotted against average intensity. These plots revealed that most erroneous heterozygous calls in inbred strains are easily distinguished from true heterozygous calls by greatly reduced average intensity. Didion suggested that genotyping algorithms that discriminate based only on contrast (such as BRLMM-P) would be unable to detect OTVs.

Thus, "off-target variants" (OTVs) tend to produce an additional genotype cluster besides the normal two or three genotypes for diploid species, AA, AB and BB, or AA, BB. This cluster can be referred to as the variant or "V" cluster or the OTV cluster. The OTV cluster samples create problems in genotype calling. These samples are often miscalled as "AB," the heterozygote cluster. According to specific embodiments, systems and methods as described herein separate this OTV cluster from the other genotype clusters more effectively than previous methods.

For example, the technique from MouseDivGenoR (Didion) package fails to detect some OTVs. The method uses an OTV score, a product of two p values for to determine OTVs. The two p values measure deviation from the center of cluster and deviation from the center of all the samples in terms of size (or intensity) dimension, respectively. Then the Didion method uses a nearest neighbor algorithm to determine the V cluster. The technique uses a stringent threshold (score>0.9999) and fails particularly when three genotype clusters exist, AA, BB, and V.

OTV Identification and Genotype Clustering

Figure 1B:
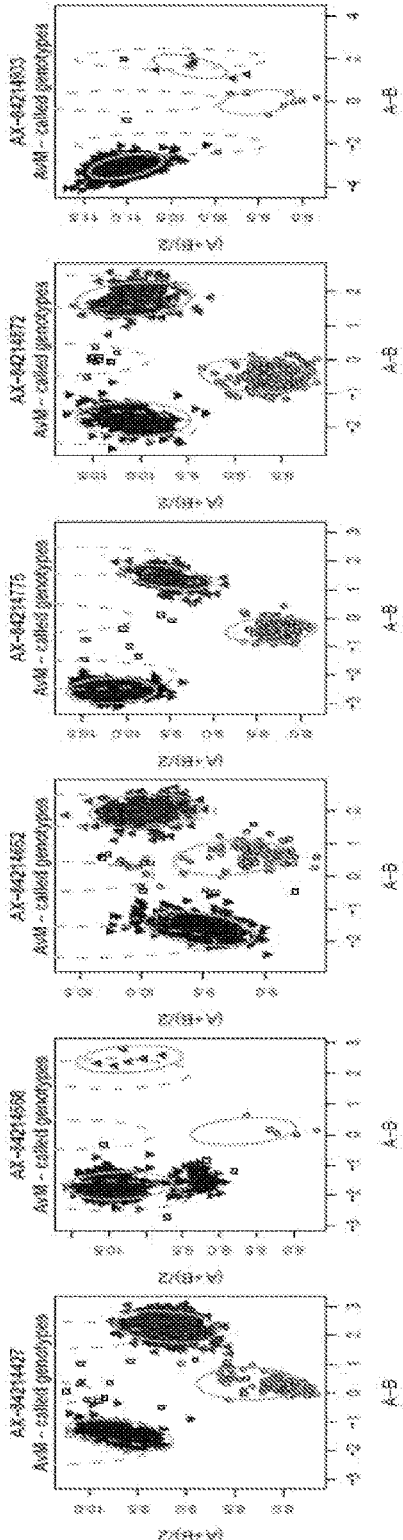
FIG. 1B provides examples of re-clustering or re-calling genotyping data after allowing for a variant cluster according to specific embodiments.
Figure 1B:
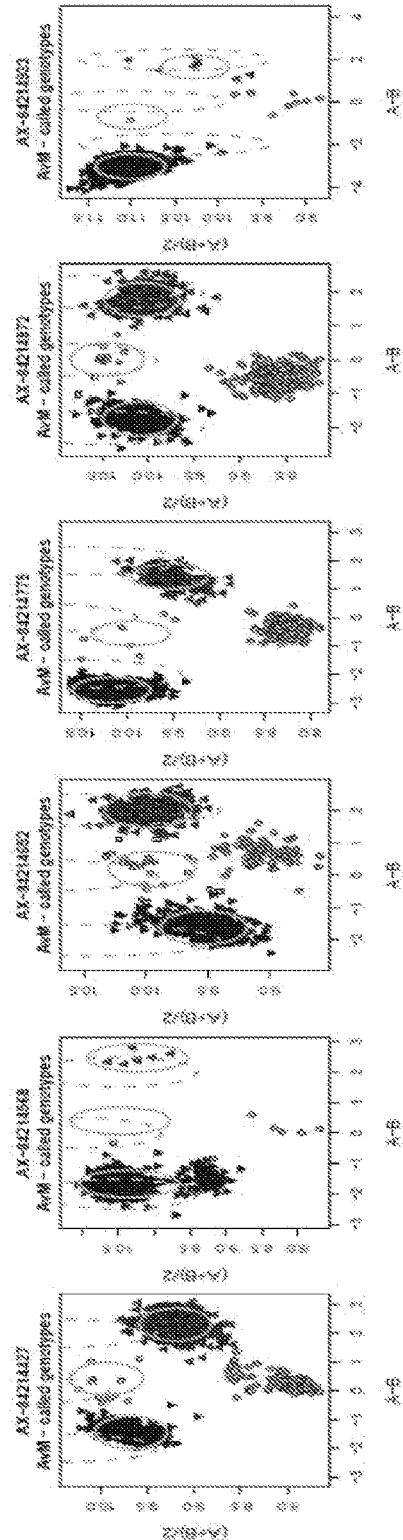

FIG. 1A-B provide examples of re-clustering or re-calling genotyping data after allowing for a variant cluster according to specific embodiments. According to specific embodiments, an OTV genotype analysis uses the posterior information from a genotype cluster analysis (e.g., from an initial cluster algorithm, such as AxiomGT1®) to initiate an expectation maximization EM algorithm or similar technique to determine whether an OTV cluster is present and to identify or call which samples are in the OTV cluster. According to specific embodiments, a method can also repeat the calls for samples in the AA, AB, and BB clusters. In particular embodiments, a post-processing technique for OTV-Typing uses a 2D EM algorithm with constraints to cluster based on both contrast and strength dimensions. In one example, the method using the posteriors from the Affymetrix Power Tool (APT) AxiomGT10 algorithm as the starting points for AA, AB, BB and OTV clusters in the EM algorithm. Then the algorithm iteratively updates sample assignments and cluster centers until convergence is reached.

Figure 2:
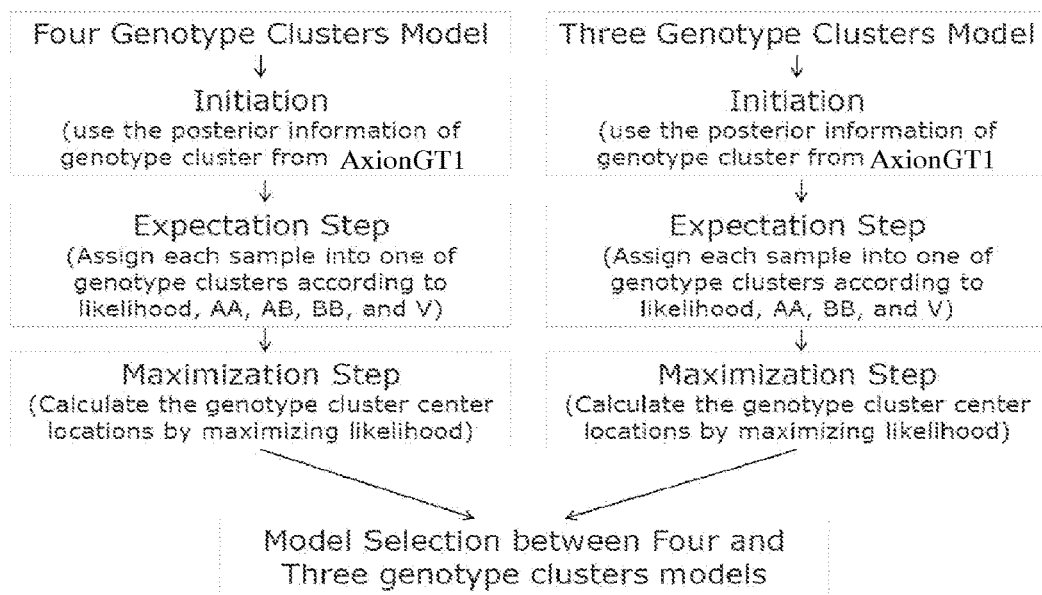
FIG. 2 illustrates workflow of an algorithm (referred to at times as OTVCaller™) according to specific embodiments, wherein two models are considered, including a three-genotype model (AA, BB, and OTV) and a four-genotype model (AA, AB, BB, and OTV).

Thus, according to specific embodiments, a statistical approach generally considering all the sample data from a probeset is used to genotype the OTVs. In one example, the posterior genotyping information generated by the automated clustering algorithm AxiomGT10 is used to initiate the 2D Baum-Welch algorithm in order to search for the optimal clustering including the possibility of an OTV cluster using both intensity and contrast information from the samples. (In the example figures provided herein, sample data is plotted with intensity on the X-axis and contrast on the Y-axis and these orientations are used in some of the description below. As is known in the art, different plots of the same data are equivalent.) As is known in the art, the 2D Baum-Welch algorithm then iteratively updates sample assignments and cluster centers until convergence is reached. An overview workflow of such a method, (referred to at times as the OTVCaller™) algorithm is illustrated in FIG. 2. (In one example embodiment, the method is implemented with other methods, including methods described herein, in a combined software package).

The AxiomGT1 algorithm is based on the BRLMM-P algorithm and incorporates a multi-channel processing method and features for pre-processing and genotype calling Clusters in this particular system are represented as two-dimensional Gaussians and resistance to non-Gaussian cluster behavior has been improved. Training data has been used to generate SNP-specific models that represent the cluster properties learned for each marker. Unlike the DMET Plus Assay, which is designed to call in a single-sample mode without adapting to the data, the AxiomGT1 default behavior uses dynamic clustering to adapt the clusters to the observed data. Although a single sample can be run by itself, more samples allow the algorithm to learn more from the training data.

Off Target Variant (OTV)

OTV SNPs or other polymorphisms according to specific embodiments are identified or genotyped using posterior genotyping information as the prior information for the genotype clusters including an OTV cluster, e.g., (AA, AB, BB and V), (AA, BB and V). An EM algorithm is applied to iteratively learn the optimal locations of centers of these clusters and make OTV calls for the OTV cluster until convergence is reached. According to specific embodiments, the method successfully identifies an OTV cluster in the presence of three genotypes AA, AB and BB or two genotypes AA and BB.

Further embodiments, use a metric for SNP probeset quality control referred to at times as heterozygote strength offset (HetSO). HetSO in an example embodiment is defined generally as the vertical distance or other distance depending on orientation (as measured by [A+B]/2 or signal size) from the center of the heterozygote cluster to the line connecting the centers of the homozygote clusters. Generally, large negative values are associated with or indicate OTV clusters. According to specific embodiments, OTVs are therefore recognized as genotypes with good cluster resolution but with a HetSO (or related value) meeting specific criteria (e.g., a threshold of HetSO<about −0.3). The criteria are customizable or adjustable according to specific embodiments.

Specific Example

A highly detailed description of a method for OTV genotyping is presented below. This description is presented for illustrative purposes. A number of possible variations will be understood to those of skill in the are have the benefits of the teachings provided herein.

One example OTV genotyping algorithm analyzes probesets one by one and proceeds generally as follows.

For a given probeset, assume that there are K genotypes, where K can be 3 (AA, BB, OTV) or 4 (AA, AB, BB, OTV). There are N samples genotyped at that SNP.

Denote $x_j$ to be contrast value of sample j (where j=1, 2, . . . , N), which is calculated as log 2(intensity from channel A)−log 2(intensity from channel B).

Denote $y_j$ to be average intensity strength of sample j, also called as "size", which is calculated as (log 2(intensity from channel A)+log 2(intensity from channel B))/2.

Denote $z_{jk}$ to be the probability that sample j belongs to genotype cluster k, where j=1, 2, . . . , N and k=1, 2, . . . , K.

Denote $a_k$ to be center location (mean) of size dimension for genotype cluster k and $m_k$ to be center location (mean) of contrast dimension for genotype cluster k.

Denote $Va_k$ to be variance of size dimension for genotype cluster k and $Vm_k$ to be variance of contrast dimension for genotype cluster k.

Denote $p_k$ to be the prior probability of assignment of any sample to genotype cluster k.

A 2D Gaussian mixture model is fitted to both the size and the contrast dimension data. It uses the Expectation-Maximization (EM) algorithm. For maximization step, the mean and variance of genotype cluster k for both size and contrast dimensions are calculated to maximize the likelihood. To initialize the EM algorithm, obtain the values from prior clustering, To estimate the maximum likelihood estimator (MLE) of contrast mean of genotype cluster k:

$$m_k = \frac{\sum_{j=1}^{N} x_j z_{jk}}{\sum_{j=1}^{N} z_{jk}}$$

The MLE of size mean of genotype cluster k is $$a_k = \frac{\sum_{j=1}^{N} y_j z_{jk}}{\sum_{j=1}^{N} z_{jk}}$$

The MLE of size variance of genotype cluster k is $$Vm_k = \frac{\sum_{j=1}^{N} (x_j - m_k)^2 z_{jk}}{\sum_{j=1}^{N} z_{jk}}$$

The MLE of size variance of genotype cluster k is $$Va_k = \frac{\sum_{j=1}^{N} (y_j - a_k)^2 z_{jk}}{\sum_{j=1}^{N} z_{jk}}$$

The MLE of probability that any sample belongs to genotype cluster k is $$p_k = \frac{\sum_{j=1}^{N} z_{jk}}{N}$$

For expectation step, the probability of sample j assigning to genotype cluster k is:

$$z_{jk} = \frac{p_k Norm(x_j, m_k, Vm_k) Norm(y_j, a_k, Va_k)}{\sum_{i=1}^{K} p_i Norm(x_j, m_i, Vm_i) Norm(y_j, a_{ki}, Va_i)}$$

The algorithm iterates the Expectation step and the Maximization step until convergence is reached. Then Bayesian Information Criteria (BIC) is used, as will be understood in the art, to select among the models with three or four genotype clusters.

Figure 3:
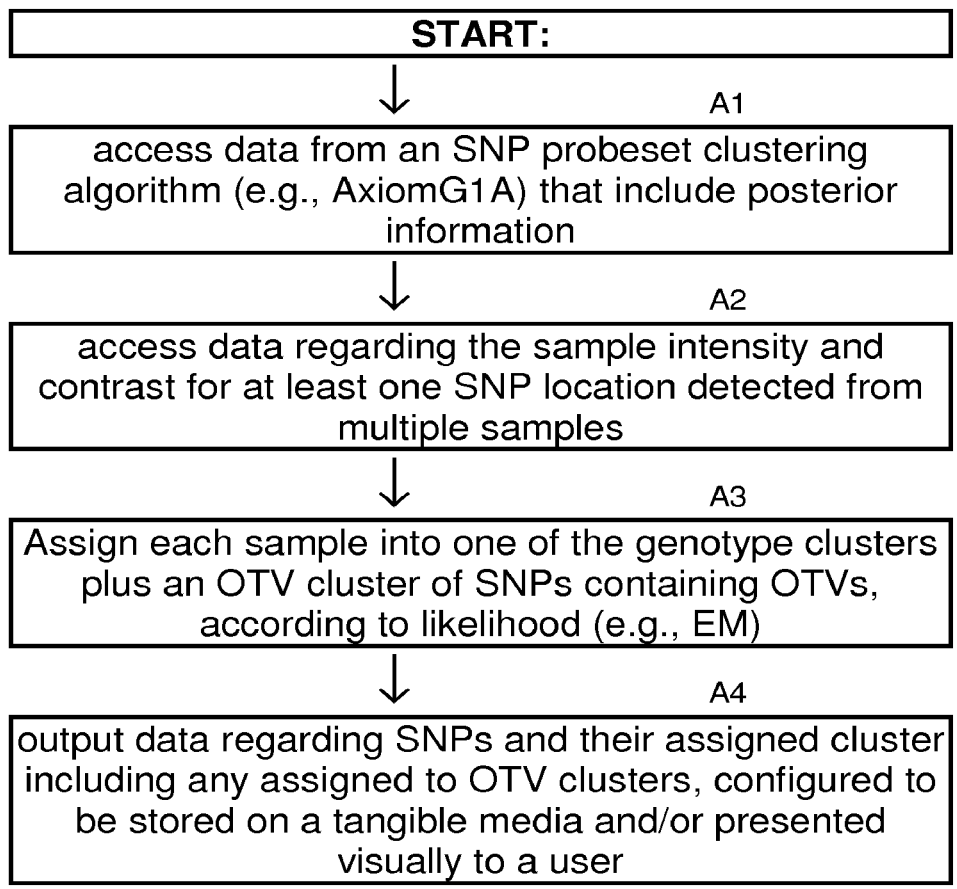
FIG. 3 is a flowchart of an example method for clustering genotyping data into genotype clusters and an OTV cluster using posterior data from a genotype clustering according to specific embodiments.

FIG. 3 is a flowchart of an example method for clustering genotyping data into genotype clusters and an OTV cluster using posterior data from a genotype clustering according to specific embodiments.

Figure 4:
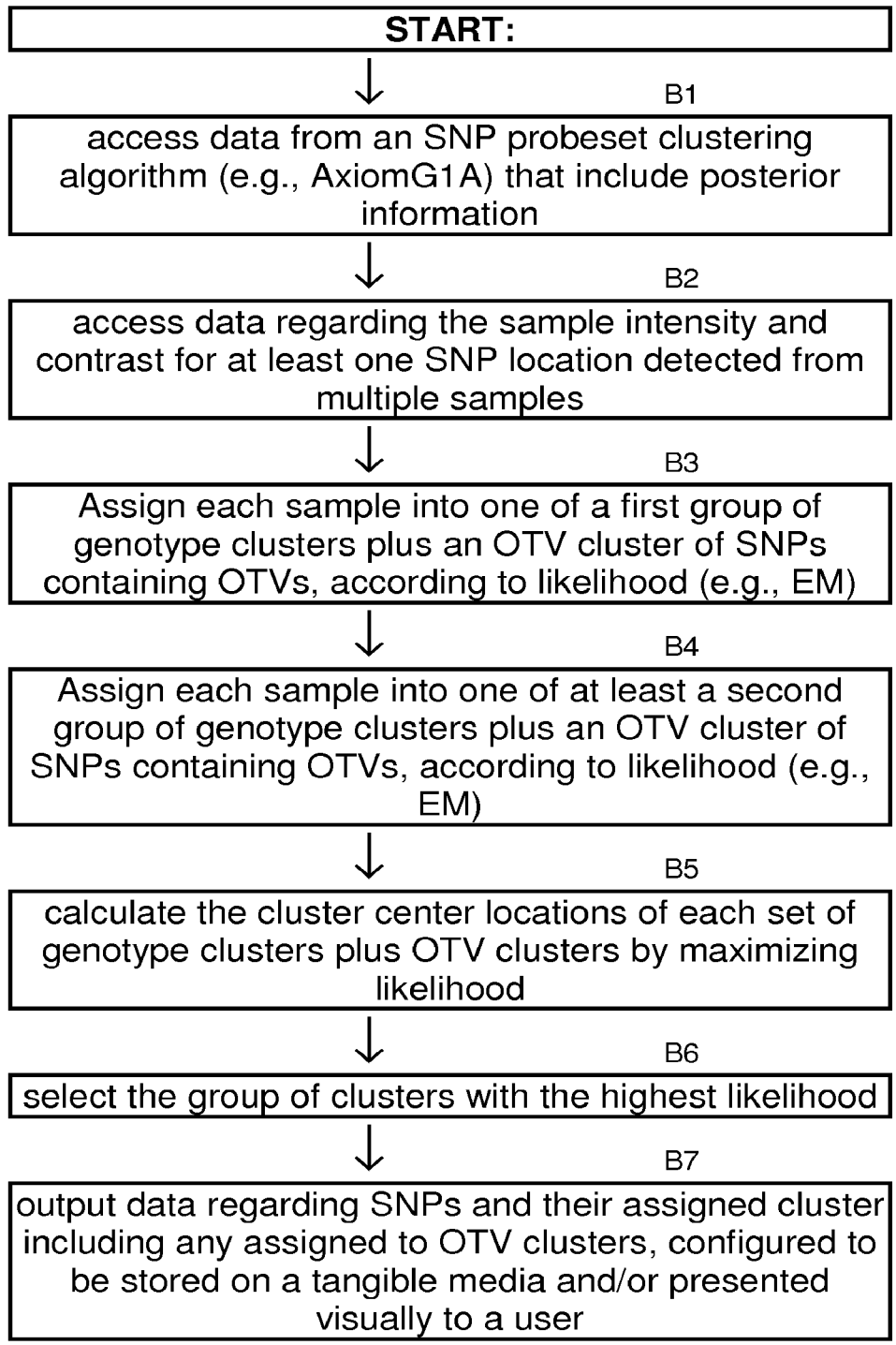
FIG. 4 is a flowchart of an example method for clustering genotyping data into genotype clusters and an OTV cluster using posterior data from a genotype clustering and evaluating more than one group of possible genotype clusters according to specific embodiments.

FIG. 4 is a flowchart of an example method for clustering genotyping data into genotype clusters and an OTV cluster using posterior data from a genotype clustering and evaluating more than one group of possible genotype clusters according to specific embodiments.

Figure 5:
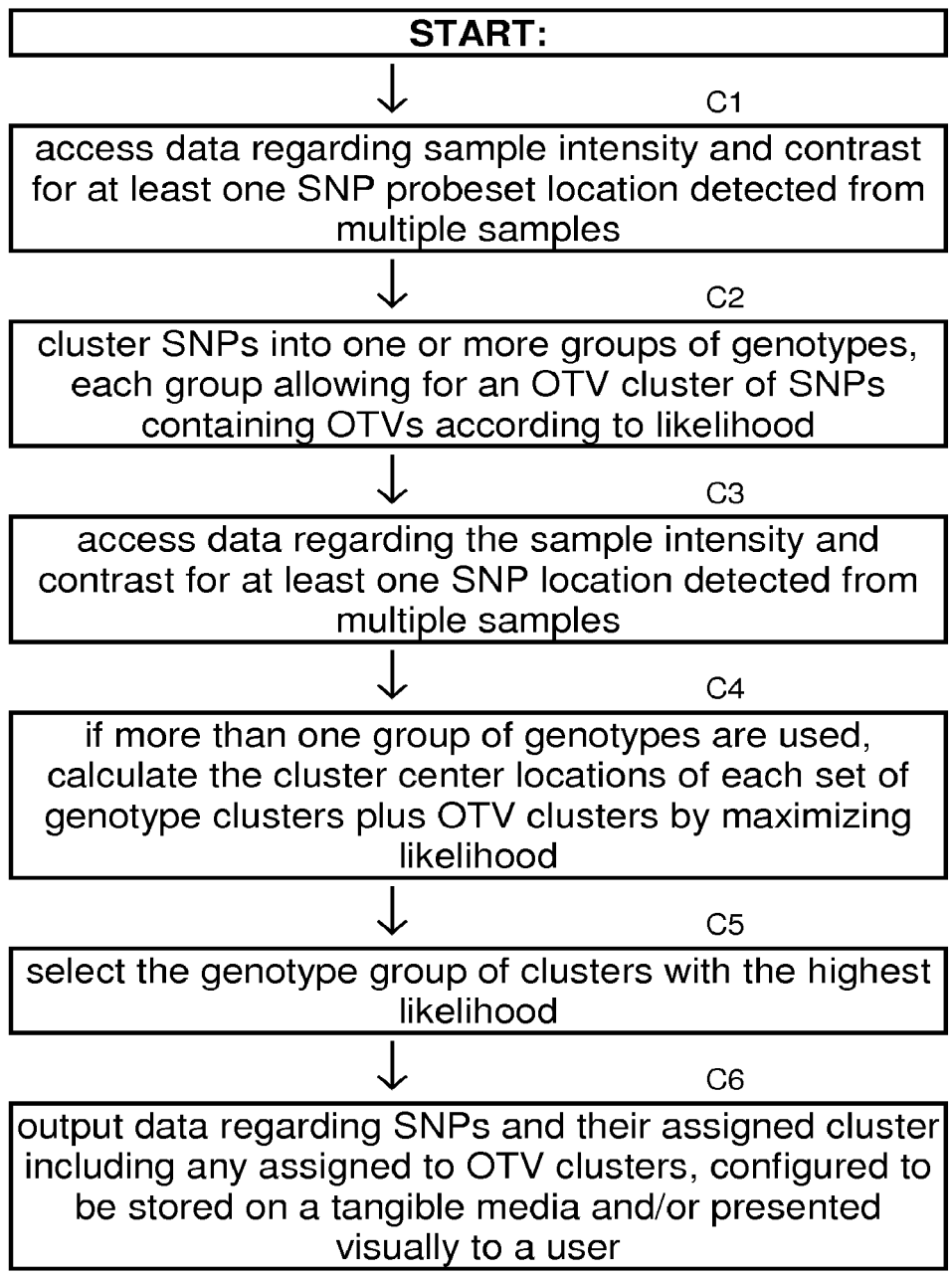
FIG. 5 is a flowchart of an example method for initially clustering genotyping data into genotype clusters and an OTV cluster and optionally evaluating more than one group of possible genotype clusters according to specific embodiments.

FIG. 5 is a flowchart of an example method for initially clustering genotyping data into genotype clusters and an OTV cluster and optionally evaluating more than one group of possible genotype clusters according to specific embodiments.

SNP Probeset Quality Control (QC) Metrics

According to further specific embodiments, a set of probeset quality control (qc) metrics detects misclustered SNPs or other polymorphisms and other properties to provide better analysis. According to specific embodiments, the set of QC metrics can include one or more of the metrics discussed below. According to further specific embodiments, one or more of these metrics are used to classify probesets into quality or characteristic classes.

Some SNP metrics have previously been used to rank probes for genotyping, see, e.g., affymetrix(.)com/support/developer/powertools/changelogNIGNETTE-WGSA-empirical-probe-ranking.html. According to specific embodiments, combinations of previously used metrics and new metrics have been developed to classify SNP probeset genotyping results into one of several classifications, including an OTV classification.

SNP Call Rate

According to specific embodiments, the SNP call rate is an indication of how many SNPs, generally across multiple samples, were called into an available genotype. It may be expressed as a percentage or ratio or decimal and while variations are possible, is generally expressed as (Samples Called/Total Samples.) In specific embodiments, SNP call rate=Number of Samples Called/N N=the number of samples over which a genotype call is attempted for the SNP. According to specific embodiments, number of samples called is the number of samples assigned a genotype call (e.g., either AA, BB or AB, AA or BB, genotypes for polyploidy, optionally genotypes including an OTV cluster) at the SNP locus. This is also generally the number of samples that do not have a "No Call" assignment. According to specific embodiments, SNP call rate (which is different than sample call rate) is a measure of both data completeness and of genotype cluster quality (at low values). Very low SNP call rates are generally due to a failure to resolve the genotype clusters, and poor cluster resolution may produce inaccurate genotypes in the samples that are called. Even if the called genotypes are correct, if the no-calls are non-randomly distributed across the genotype clusters, this missing information may lead to false positive associations in a genome-wide association (GWA) study.

FLD

Figure 6A:
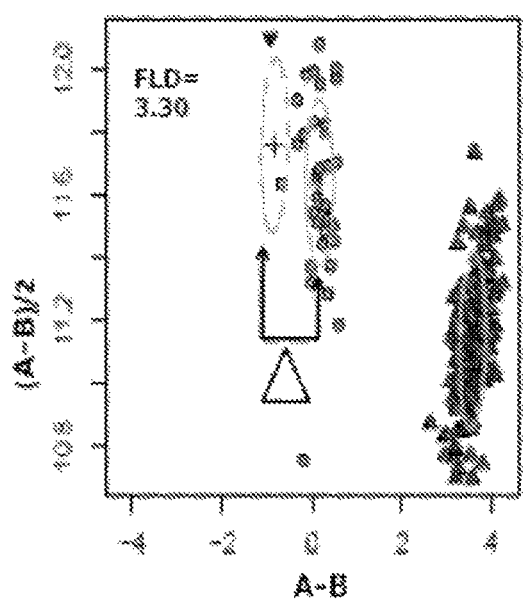
FIG. 6A illustrates an example of a SNP genotyping data result with a high call rate but a low FLD value according to specific embodiments.
Figure 6B:
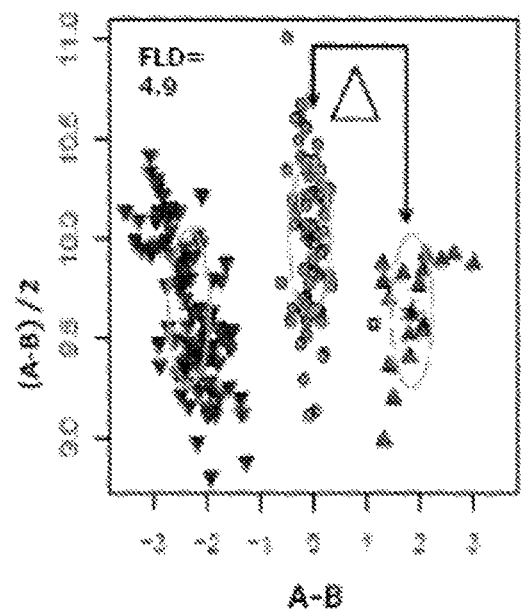
FIG. 6B illustrates well-clustered SNP genotyping data with well-separated genotype cluster centers according to specific embodiments.

Fisher's Linear Discriminant is a well-known statistical method generally used to find a combination of features that characterizes or separates two or more classes of objects or events and previously used to characterized probesets. According to specific embodiments, Fisher's Linear Discriminant (FLD) is applied to the genotype clusters and is a measure of the cluster quality of a probeset. It is used with other parameters and metrics as discussed herein to characterize probesets. High-quality clusters have well-separated centers (with respect to other clusters) and little variance about the center of the cluster (i.e., the clusters are narrow). High-quality clusters can be identified in cluster plots by examining the shape and separation of the SNP probeset posteriors that are produced during genotyping. The posteriors (e.g., the data or a diagrammatic representation (e.g., an ellipse)] that identifies the cluster location and variance of each genotype cluster that is produced by the genotyping algorithm) for the individual clusters should be narrow and have centers that are well separated from each other. It is recommended that probesets with an FLD value less than a threshold (e.g., 3.6 in one example system) be removed from the study prior to downstream analysis. SNP call rates and FLD values are normally correlated, but in some cases FLD will detect problems not detected by the SNP call rate metric. FIG. 6A illustrates an example of a SNP genotyping data result with a high call rate but a low FLD value and in contrast, B illustrates well-clustered SNP genotyping data with well-separated genotype cluster centers. In FIG. 6A, the clustering algorithm has found the location of the BB cluster too close to the AB cluster and has assigned two data points (which are actually AB genotypes) to the BB genotype cluster (blue). The misclustering event is detected by measuring the FLD value for this SNP because the mislabeled BB cluster center is very close to the AB cluster center, thus producing an FLD value of 3.30. In contrast, the well-clustered The SNP in FIG. 6B has well-separated genotype cluster centers and an FLD value of 4.9 FLD in this figure is basically the smallest difference between the cluster centers as indicated by the triangles. BB cluster samples are shown as blue inverted triangles. AA cluster samples are shown as red triangles. AB cluster samples are shown as yellow circles and No Calls are shown as grey boxes.

According to specific embodiments, the FLD is computed directly from the genotypes and the data, consisting of the distance between cluster centers divided by the standard deviation within clusters. This measures the separation between clusters directly in terms of cluster variation. While a useful metric, it is difficult to interpret when genotypes are missing for one or more clusters (and is filled in by prior information). In specific examples, there are 3 FLD values, one for each cluster pair. Generally, the largest FLD is the 'best'.

FLDAH-FLD between AA and AB
FLDHB-FLD between AB and BB
FLDAB-FLD between AA and BB According to specific embodiment, an FLD for the genotype clusters of an SNP can be determined generally as follows:

$$(FLD)=\text{Min}(I=AA,BB) \{M_{AB}-M_I/sd\}$$

Where: $M_{AB}$=center of heterozygous cluster in log ratio dimension, $M_{AA}$, $M_{BB}$=center of homozygote A, B cluster in log ration dimension; sd=square root of variance pooled across all three distributions. FLD is undefined if either of the two clusters (AB and either AA or BB) is unpopulated.

Heterozygous Cluster Strength Offset (HetSO)

Figure 7A:
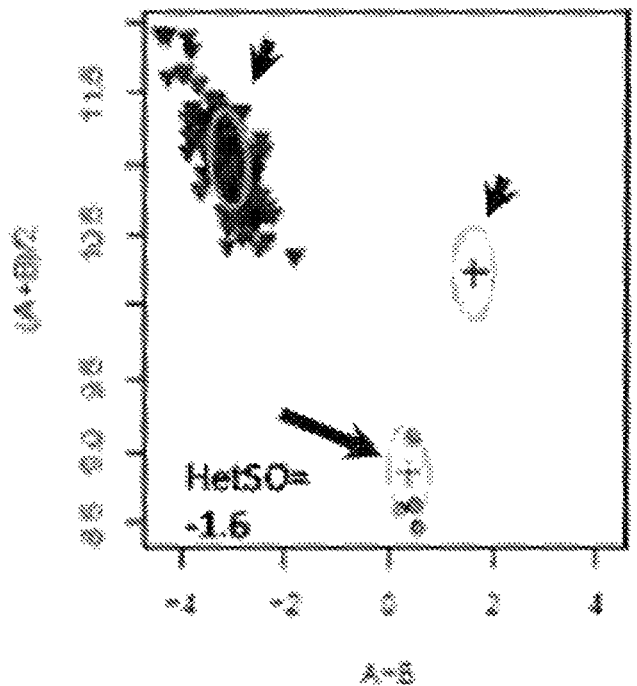
FIG. 7A illustrates an example of SNP genotyping data, where sequence mismatches between the sample and the reference genome have produced a HetSO value outside of the acceptable range.
Figure 7B:
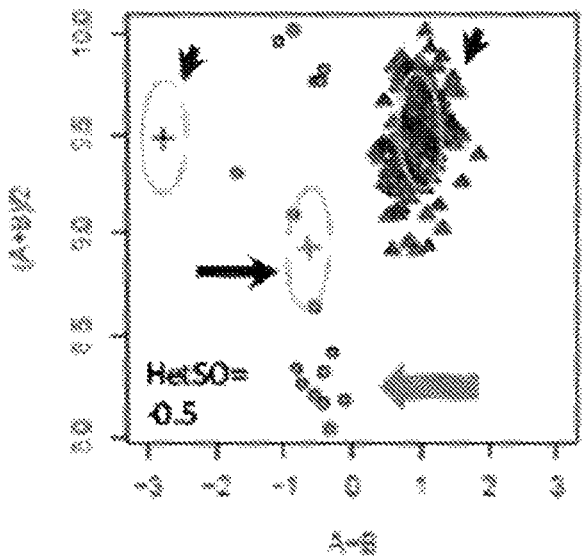
FIG. 7B illustrates an example of SNP genotyping data, where sequence mismatches between the sample and the reference genome have produced a HetSO value outside of the acceptable range.

Heterozygous Cluster Strength Offset (HetSO) is defined according to specific embodiments as the vertical distance (as measured by [A+B]/2 or signal size) from the center of the Heterozygous (e.g. AB) cluster to the line connecting the centers of the homozygous clusters (e.g., AA, BB). Low HetSO values are produced by misclustering events and by inclusion of samples with high degree of mismatches relative to the reference genome (i.e., samples with variation in the genome region against which the 30 mer SNP probe sequence was designed). FIGS. 7A and B illustrate an example of SNP genotyping data, where sequence mismatches between the sample and the reference genome have produced a HetSO value outside of the acceptable range. When there is a high degree of mismatch between the sample and reference genome, the A and B intensities produced by the samples are low, and fall into the location of the heterozygous cluster. If enough samples fall into this heterozygous cluster location, then the clustering algorithm incorrectly calls these cases as AB (instead of No Calls). These samples can be identified by low HetSO values. Visually, the average signal value (as measured along the y-axis) is much lower for the heterozygous cluster than for the homozygous clusters. Generally, there is a recommendation to remove any SNPs with HetSO less than −0.1 or some other threshold from the downstream genotyping analysis.

$$HetSO=A_{AB}-A_{BB}+(A_{AA}-A_{BB})\times(M_{AB}-M_{BB}/M_{AA}-M_{BB})$$

Where $(M_{AA}, A_{BB})$=center of AA cluster, etc.

Homozygote Ratio Offset (HomRO)

Homozygote Ratio Offset (HomRO) is the location, in the contrast dimension (e.g., the X axis in example figures provided herein) of the homozygous genotype cluster center that is closest to zero (the heterozygote position), and/or most likely to be misplaced. If the homozygous cluster is on the expected side of zero (the heterozygous position), the value is positive, otherwise negative. A low or negative value tends to indicate that the genotyping algorithm has mislabeled the clusters, producing incorrect genotype cells. Considering only populated homozygote clusters:

If both are on the proper side of zero contrast, the HomRO=min($X_{AA}$, abs($X_{BB}$)), where $X_{AA}$=the posterior mean of the AA cluster, and $X_{BB}$=the posterior mean of the BB cluster.

If both are positive (on the AA side of zero), HomRO=−$X_{BB}$ (negative indicates "wrong side")

If both are negative (on the BB side of zero), HomRO=$X_{AA}$.

Figure 8A:
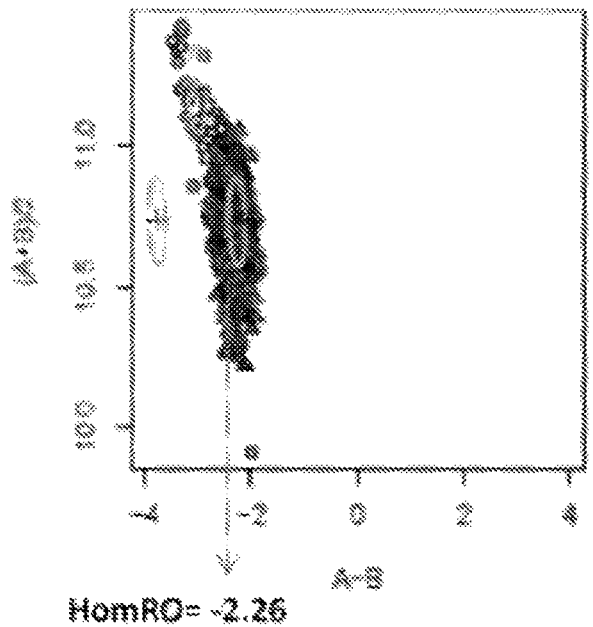
FIG. 8A illustrates an example of SNP genotyping data misclustered and with a negative HomRO.
Figure 8B:
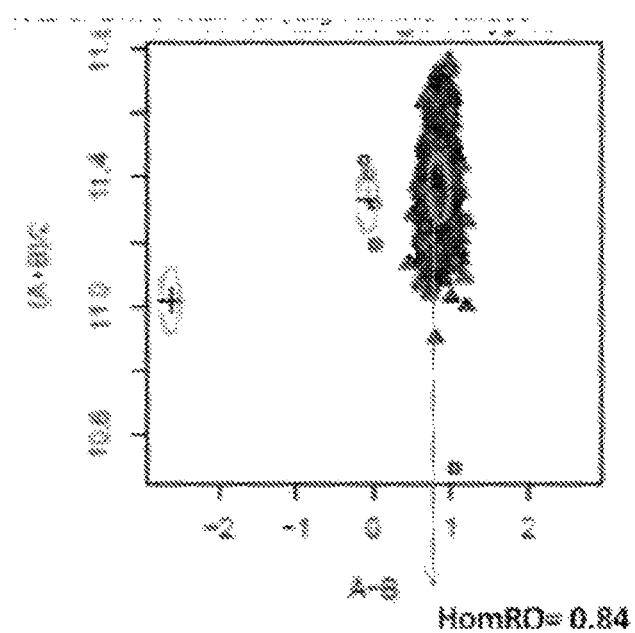
FIG. 8B illustrates an example of well clustered SNP genotyping data.

FIG. 8A illustrates an example of SNP genotyping data misclustered and with a negative HomRO value and B illustrates a well clustered SNP genotyping data. In this example the HomRO value is −2.26. The putative AA (red) genotype cluster is on the wrong/negative side in contrast space. As a consequence of incorrectly identifying most of the data points as AA, the genotyping algorithm has additionally produced a cluster split and labeled some of the points (all actually BB) as AB, where AA (red) genotype cluster is positive (0.84) as expected.

In a specific example embodiment, one or more of these metrics are calculated for a plurality of available probesets from a probeset cluster data file. FIG. 9A-B illustrate an example output of a logic routine that determines genotyping data quality metrics or probeset assay data quality metrics according to specific embodiments.

SNP Type Classification

Figure 10:
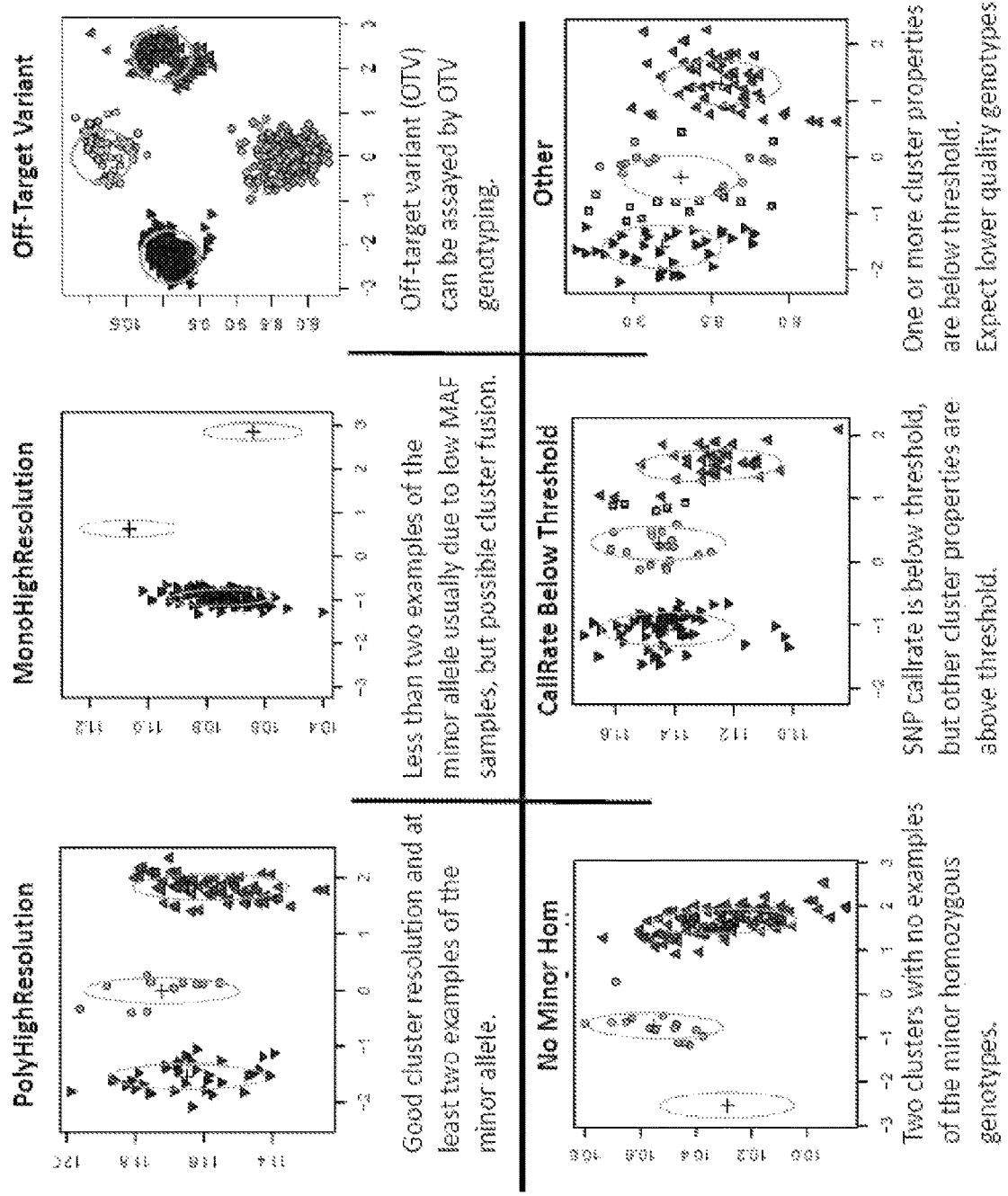
FIG. 10 is an illustration of six genotyping data type classification according to specific embodiments.

FIG. 10 is an illustration of six genotyping data type classification according to specific embodiments. In one example, this classification is enabled with logic routines as part of a larger SNP analysis system, (e.g., Axiom Analysis Workflow®). For example, the illustrated classification examples were extracted from Maize. As shown in the figure, the six example classifications are:

(1) PolyHighResolution, characterized by good cluster resolution, and at least 2 examples of the minor allele. According to specific embodiments, these can be understood as converted polymorphic SNPs.

(2) MonoHighResolution, characterized by less than 2 sample points of the minor allele usually due to low MAF samples, but possible cluster fusion/compression According to specific embodiments, these can be understood as converted monomorphic SNPs.

(3) Off Target Variant (OTV), where an OTV cluster has been called as discussed herein. According to specific embodiments, these probesets give very low signal intensity in some individuals. Often the result of a nearby destabilizing SNPs or a small deletion.

(4) No Minor Homozygote, characterized by two clusters with no examples of the minor homozygous genotypes. According to specific embodiments, these can be understood as 2 cluster SNPs found in homozygous inbred individuals.

(5) Call Rate Below Threshold, characterized by SNP call rate below threshold, but other cluster properties are above threshold.

(6) Other, wherein one or more cluster properties are below threshold and therefore lower quality genotypes are likely. These are effectively unconverted SNPs.

Example Rules for Identifying SNP Types

According to specific embodiments, one or more SNP types are defined in terms of quality metrics as discussed above and other parameters of SNPs. An example of a set of SNP types and example rules for defining them according to specific embodiments is provided below. Not all rules may be necessary or used for defining the classifications.

I. PolyHighResolution

SNP Cluster passes all thresholds as discussed below.

II. MonoHighResolution

SNP Cluster passes all thresholds, except nMinorAllele

III. Off Target Variant (OTV)

SNP(s) have good cluster properties, with the exception of a cluster in the OTV position.
FLD>=threshold (e.g., 3.6)
HomRO>=threshold
HomHet==1, if set
Heterozygous cluster is populated
HetSO<threshold (e.g., −0.3)
Homozygote cluster(s) is offset from zero in the contrast dimension IV. CallRateBelowThreshold SNP Cluster passes all thresholds, except Call Rate, with nMinorAllele ignored V. NoMinorHom Only if HomHet is set
SNP Cluster passes all thresholds and is a two cluster SNP (one Homozygous and one Heterozygous), with HetSO and nMinorAllele ignored "No Minor Hom" Classification Considerations When genome is polyploid, unambiguous assignment of the genotype for a 2 cluster SNP ("NoMinorHom" SNP classification) can be challenging when one of the cluster in the diploid heterozygous position without prior knowledge of the sample genetics (rapeseed example) However, when lines are in-bred, heterozygous genotypes assignment without examples of both homozygous genotypes may be unexpected (e.g., for wheat example.)

Example Thresholds for PolyHighResolution SNPs

Threshold values for the parameters described above and for parameters as known in the art as used in the SNP classifier as described above. These values may be varied in different systems and for a number of different reasons. One example set of values is as provided below.

CR.cut-Call Rate threshold; usually about 95-97
FLD.cut-FLD threshold; usually about 3.6
HetSO.cut-HetSOthreshold usually about −0.1
HomRO2.cut-HomROthreshold for 2-cluster SNPs; usually about 0.3
HomRO3.cut-HomROthreshold for 3-cluster SNPs; usually about −0.9
nMinorAllele-Number of Minor Alleles; usually two
HomHet.flag=FALSE Using SNP Classifications to Select SNP Probe Sets According to specific embodiments, the classifications described above can be used to select a best probe set. A "best" probeset is generally selected in various situations where more than one probeset is available for an SNP, as would be understood in the art. Probeset selection is done in many different situations and according to many different criteria.

According to specific embodiments as described herein, one method for probeset selection is to (1) Categorize probesets into the available types (e.g., the six types described above). For an SNP, select a probeset that has the highest priority as categorized by the types.

In a specific embodiment, the type priority is: PolyHighResolution, MonoHighResolution, OTV, CallRateBelowThreshold, NoMinorHom, Other. Call Rate and FLD are used to break ties.

Example Software Package

According to further specific embodiments, one or more of the above methods is included in a software package to automatically genotype polymorphisms from array data or similar genotype data. Such a software package may include initial clustering or such a software package may be a post-processing package applied after initial clustering. In either case, according to specific embodiments, such a software package provides fully automated probeset selection for polymorphisms as described herein. According to further embodiments, such a software package identifies the presence of OTV probes using statistical characteristics of the majority or all of the sample data from the probe.

Figure 11:
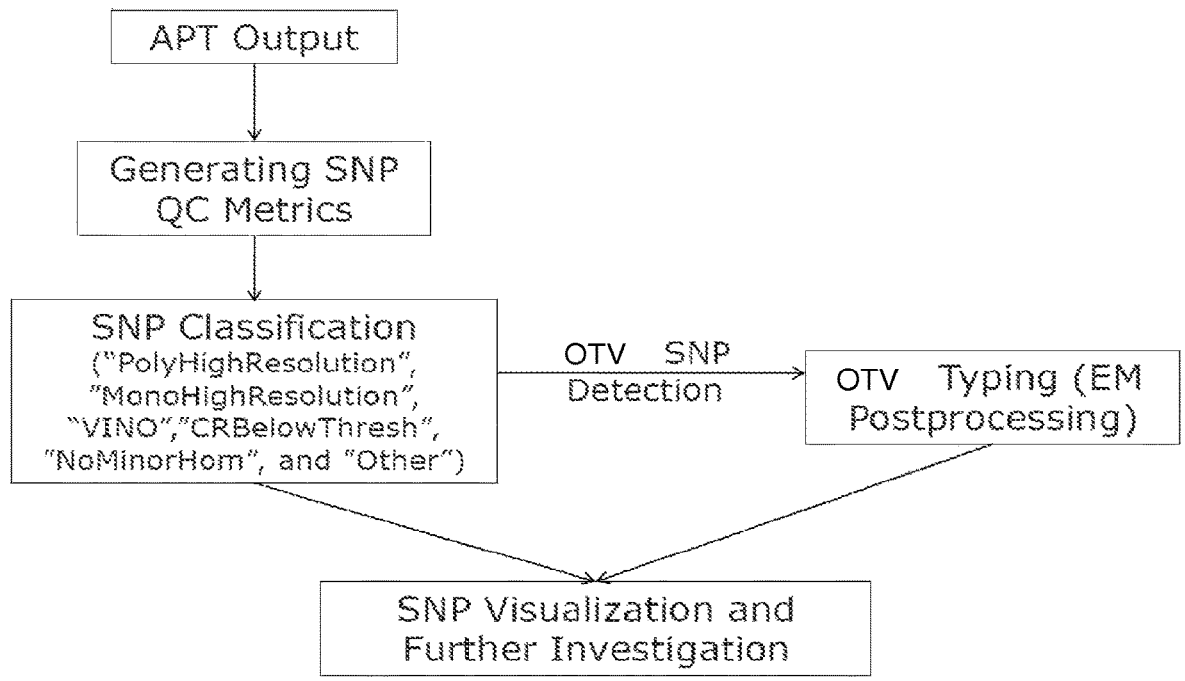
FIG. 11 is a flowchart illustrating overall steps for polymorphism (e.g., SNP) analysis, including classification and OTV identification according to specific embodiments.

SNPolisher™ is one particular example of such a software system, in this case designed to post-process genotyping results by Affymetrix Axiom Genotyping Arrays, though other genotyping data can be handled so long as the data is presented in the formats used by the program. Alternatively, SNPolisher can be modified or customized to work with any comparable data sets. FIG. 11 is a flowchart illustrating overall steps for polymorphism (e.g., SNP) analysis, including classification and OTV identification according to specific embodiments.

Figure 12:
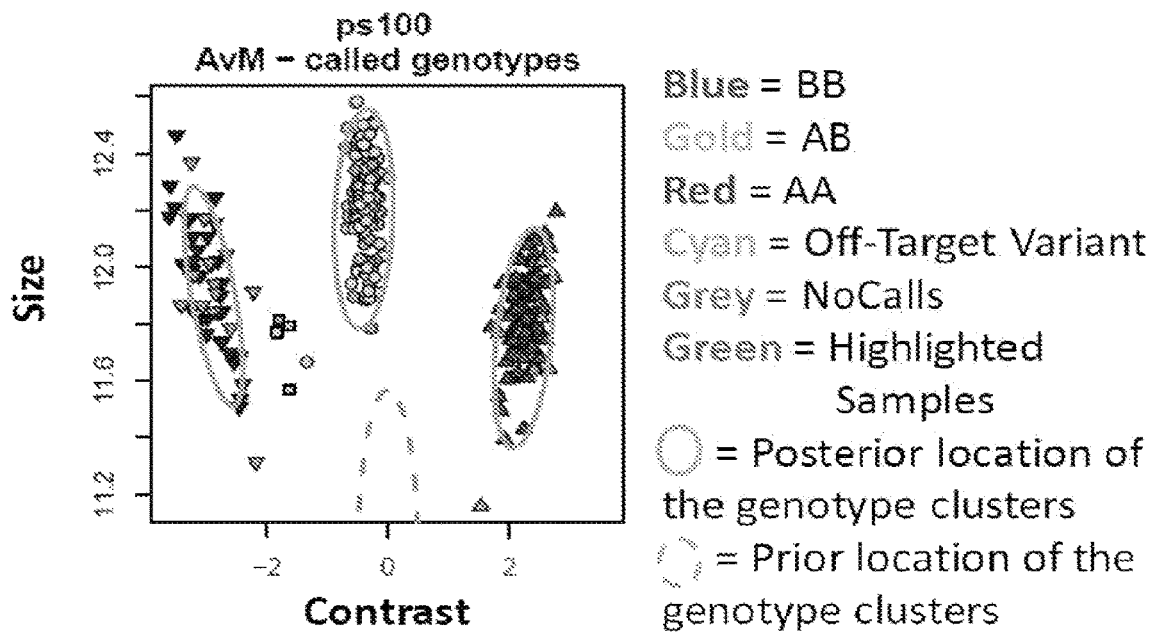
FIG. 12 shows an example of visualization of a SNP genotyping data probeset results with interpretations using a logic routing according to specific embodiments.

According to specific embodiments, SNPolisher contains four major functions (1) SNP Quality Control (QC) Metrics Generation, (2) SNP Classification based on QC metrics, (3) SNP Genotype Cluster Visualization, and (4) Off-target variant (OTV) genotyping. Input files in an example system are the standard genotyping output files from Affymetrix Power Tools (APT) or Genotyping Console (GTC) for the Axiom arrays (note ps2snp.file is in the library file package). SNPolisher calculates the QC metrics for each SNP/probeset to determine the probeset's quality and optionally classifies SNPs/probesets into six major categories or types as described above. SNPolisher can select the best probeset to represent a SNP if multiple probesets exist for a specific SNP. SNPolisher can also generate the visualization for each SNP/probeset to evaluate its quality. FIG. 12 shows an example of visualization of a SNP genotyping data probeset results with interpretations using a logic routing according to specific embodiments. Third, it can OTV genotype those OTV SNPs to produce AA, AB, BB and OTV genotype clusters.

According to specific embodiments, SNPolisher™ is implemented as a well-known statistical programming module referred to as an R package. SNPolisher™ is at times distributed with two test data sets that are used as examples to describe operations below. Testdata1 contains genotype data from a diploid species with 500 probesets genotyped in 300 samples. Testdata2 contains genotype data from an allo-hexaploid species with 800 probesets genotyped in 100 samples. Below is described in general terms the usage of the four major functions using these test data-sets.

Quality Control Metrics Generation and Probeset Classifications

In an example system, metrics and classification are generated using two input files, e.g., "AxiomGT1.snp-posteriors.txt" containing the posterior information for each genotype cluster, and the other is "AxiomGT1.calls.txt" containing inferred genotypes. QC metrics generation and probeset classifications are performed generally as described above. One example system uses and additional, 7.sup.th classifications, "Hemizygous" to indicate SNPs on chrY/chrW/Mito.

Hardware

Systems, methods, and products to address these and other needs are described herein with respect to illustrative, non-limiting, implementations. Various alternatives, modifications and equivalents are possible. For example, certain systems, methods, and computer software products are described herein using exemplary implementations for analyzing data from arrays of biological materials made by spotting or other methods such as photolithography or bead based systems. However, these systems, methods, and products may be applied with respect to many other types of probe arrays and, more generally, with respect to numerous parallel biological assays produced in accordance with other conventional technologies and/or produced in accordance with techniques that may be developed in the future. For example, the systems, methods, and products described herein may be applied to parallel assays of nucleic acids, PCR products generated from cDNA clones, proteins, antibodies, or many other biological materials. These materials may be disposed on slides (as typically used for spotted arrays), on substrates employed for GENECHIP™ arrays, or on beads, optical fibers, or other substrates or media, which may include polymeric coatings or other layers on top of slides or other substrates. Moreover, the probes need not be immobilized in or on a substrate, and, if immobilized, need not be disposed in regular patterns or arrays. For convenience, the term "probe array" will generally be used broadly hereafter to refer to all of these types of arrays and parallel biological assays.

An embodiment of a method of analyzing data from processed images of biological probe arrays is described that comprises receiving one or more data files comprising a plurality of intensity values associated with a probe on a biological probe array or comprising cluster assignments from or other output derived from such data; and assigning a plurality of genotype calls using a distance of the one or more intensity values from the posterior estimate.

The above embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to other embodiments and/or implementations. In addition, any one or more function, step, operation, or technique described elsewhere in this specification may, in alternative implementations, be combined with any one or more function, step, operation, or technique described in the summary. Thus, the above embodiment and implementations are illustrative rather than limiting.

Creating Probesets and Assays

It is generally well known that the method involves extracting genomic DNA from samples, digesting genomic DNA using restriction enzymes, labeling DNA fragments for hybridization to the probes on the chip. After hybridization, the chips are washed and scanned and a digital image is taken. For each probeset, summarize pixels to probeset intensities. This produces the raw data for the SNP analysis.

Various methods are used for genotype calling: plot each SNP in two dimensions (A & B allele intensities), though not every SNP looks alike Specific methods to call genotypes include Affymetrix Birdseed, CRLMM, Affy 500 k: Chiamo.

Various embodiments of the present invention provide methods and/or systems for probeset genotyping and characterization that can be implemented on a general purpose or special purpose information handling appliance or logic enabled system, such as a laboratory or diagnostic or production system, using any suitable programming language such as R, Java, C++, C#, Cobol, C, Pascal, Fortran, PL1, LISP, assembly, etc., and any suitable data or formatting specifications, such as HTML, XML, dHTML, TIFF, JPEG, tab-delimited text, binary, etc. In the interest of clarity, not all features of an actual implementation are described in this specification. It will be understood that in the development of any such actual implementation (as in any software development project), numerous implementation-specific decisions must be made to achieve the developers' specific goals and subgoals, such as compliance with system-related and/or business-related constraints, which will vary from one implementation to another. Moreover, it will be appreciated that such a development effort might be complex and time-consuming, but would nevertheless be a routine undertaking of software engineering for those of ordinary skill having the benefit of this disclosure.

Embodiment in a Programmed Information Appliance

Figure 13:
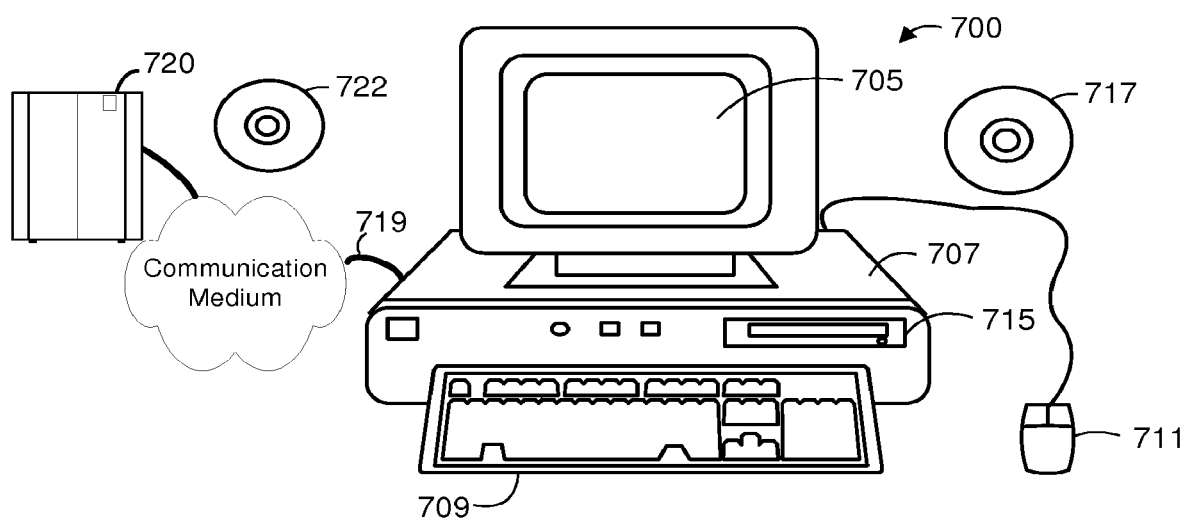
FIG. 13 is a block diagram showing a representative example logic device in which various aspects of the present invention may be embodied.

FIG. 13 is a block diagram showing a representative example logic device in which various aspects of the present invention may be embodied. As will be understood to practitioners in the art from the teachings provided herein, the invention can be implemented in hardware and/or software. In some embodiments of the invention, different aspects of the invention can be implemented in either client-side logic or server-side logic. As will be understood in the art, the invention or components thereof may be embodied in a fixed media program component containing logic instructions and/or data that when loaded into an appropriately configured computing device cause that device to perform according to the invention. As will be understood in the art, a fixed media containing logic instructions may be delivered to a user on a fixed media for physically loading into a user's computer or a fixed media containing logic instructions may reside on a remote server that a user accesses through a communication medium in order to download a program component.

FIG. 13 shows an information appliance (or digital device) 700 that may be understood as a logical apparatus that can read instructions from media 717 and/or network port 719, which can optionally be connected to server 720 having fixed media 722. Apparatus 700 can thereafter use those instructions to direct server or client logic, as understood in the art, to embody aspects of the invention. One type of logical apparatus that may embody the invention is a computer system as illustrated in 700, containing CPU 707, optional input devices 709 and 711, disk drives 715 and optional monitor 705. Fixed media 717, or fixed media 722 over port 719, may be used to program such a system and may represent a disk-type optical or magnetic media, magnetic tape, solid state dynamic or static memory, etc. In specific embodiments, the invention may be embodied in whole or in part as software recorded on this fixed media. Communication port 719 may also be used to initially receive instructions that are used to program such a system and may represent any type of communication connection.

The invention also may be embodied in whole or in part within the circuitry of an application specific integrated circuit (ASIC) or a programmable logic device (PLD). In such a case, the invention may be embodied in a computer understandable descriptor language, which may be used to create an ASIC, or PLD that operates as herein described.

The general structure and techniques, and more specific embodiments that can be used to effect different ways of carrying out the more general goals are described herein.

Although only a few embodiments have been disclosed in detail above, other embodiments are possible and the inventor(s) intend these to be encompassed within this specification. The specification describes specific examples to accomplish a more general goal that may be accomplished in another way. This disclosure is intended to be exemplary, and the claims are intended to cover any modification or alternative that might be predictable to a person having ordinary skill in the art. For example, While Affymetrix™ arrays are described in the embodiments, other embodiments may use other kinds of genotyping devices or systems.

Also, the inventors intend that only those claims which use the words "means for" are intended to be interpreted under 35 USC 112, sixth paragraph. Moreover, no limitations from the specification are intended to be read into any claims, unless those limitations are expressly included in the claims. The computers described herein may be any kind of computer, either general purpose, or some specific purpose computer such as a workstation. The computer may be an Intel (e.g., Pentium or Core 2 duo) or AMD based computer, running Windows XP or Linux, or may be a Macintosh computer. The computer may also be a handheld computer, such as a PDA, cellphone, or laptop.

The programs may be written in C or Python, or Java, Brew or any other programming language. The programs may be resident on a storage medium, e.g., magnetic or optical, e.g. the computer hard drive, a removable disk or media such as a memory stick or SD media, wired or wireless network based or Bluetooth based Network Attached Storage (NAS), or other removable medium, or other removable medium. The programs may also be run over a network, for example, with a server or other machine sending signals to the local machine, which allows the local machine to carry out the operations described herein.

Where a specific numerical value is mentioned herein, it should be considered that the value may be increased or decreased by 20%, while still staying within the teachings of the present application, unless some different range is specifically mentioned. Where a specified logical sense is used, the opposite logical sense is also intended to be encompassed.

What is claimed:

1. A method of genotyping a single nucleotide polymorphism (SNP), the method comprising:
    obtaining, using a plurality of probesets, sample data for a biological sample at a given SNP location;
    accessing, using one or more processors, genotype clustering data from a plurality of samples from a probeset location, the genotype clustering data comprising genotype cluster calls for the plurality of samples, genotype cluster centers, and variance information for each genotype cluster;
    accessing, using the one or more processors, contrast and intensity data comprising information for a probeset location across a plurality of samples;
    clustering, using the one or more processors, based on the genotype clustering data and the contrast and intensity data, the sample data in both contrast and intensity dimensions, allowing for an OTV genotype cluster;
    searching and iteratively updating, using the one or more processors, genotyping call assignments of the sample data to converged clusters and cluster centers in accordance with at least one convergence algorithm, wherein searching and iteratively updating the genotyping call assignments includes identifying the OTV genotype cluster;
    categorizing, using the one or more processors, each of a plurality of probesets used for obtaining the sample data into one of a plurality of data type classifications based on the converged clusters and cluster centers, the plurality of data type classifications having priority values relative to each other;
    selecting, using the one or more processors, a probeset of the plurality of probesets having a highest priority value data type classification of the probesets categorized; and
    creating a probeset for genotyping the SNP based on the selected probeset, wherein creating the probeset comprises extracting genomic DNA from samples, digesting genomic DNA using restriction enzymes, and labeling DNA fragments for hybridization to allelic probes on a probe array.

2. The method according to claim 1 wherein identifying the OTV genotype cluster is not based on characteristics of any single sample.

3. The method according to claim 1 wherein said searching and said iteratively updating are performed as part of an expectation maximization.

4. The method according to claim 1 wherein said searching and said iteratively updating use portions of sample intensity data that were not used to generate said genotype clustering data.

5. The method according to claim 1 wherein said searching and iteratively updating give sample intensity data more weight than was used for clustering said genotype clustering data.

6. The method according to claim 1 further comprising:
    determining a distance from the a center of a heterozygote cluster to a line connecting homozygote clusters when said samples are plotted according to contrast and intensity;
    comparing the distance to a threshold; and
    labeling as OTV clusters, clusters characterized by good cluster resolution according to a plurality of cluster parameters and by said distance exceeding a threshold.

7. The method according to claim 6 wherein said distance is referred to as a heterozygote strength offset (HetSO).

8. The method according to claim 1 further comprising:
    determining if samples outside of a populated OTV cluster constitute a genotype.

9. The method according to claim 1 wherein the genotype clustering data is generated by an automated clustering algorithm comprising one or more selected from the group: AxiomGT1, BRLMM-P, or any other suitable clustering algorithm.

10. The method according to claim 1 wherein said searching and iteratively updating is performed by a clustering algorithm selected from the group: Expectation-Maximization (EM), 2D Baum-Welch, Viterbi, HMM analysis.

11. The method according to claim 1 further comprising: distinguishing heterozygotes clusters from OTV clusters.

12. The method according to claim 1 further comprising:
    determining a cluster is an OTV cluster when:
    the samples overall have good genotype cluster properties according to one or more cluster parameters, except for a cluster in an OTV position;

Fishers linear discriminant (FLD) of the cluster is greater than or equal to a threshold;
HomRO is greater than or equal to threshold;
homozygote cluster(s) is offset from zero in the contrast dimension; and
HetSO is less than or equal to a threshold.

13. The method according to claim 1 further comprising:
determining a cluster is an OTV cluster when:
the initial sample clusters have good genotype cluster properties according to one or more cluster parameters, except for a cluster with a HetSO value less than or equal to a threshold;
Fishers linear discriminant (FLD) of the cluster is greater than or equal to a threshold;
HomRO is greater than or equal to threshold;
homozygote cluster(s) is offset from zero in the contrast dimension; and
HetSO is less than or equal to a threshold.

14. The method according to claim 1 further comprising:
selecting between a plurality of genotype cluster models by, for each model:
initiating the model by using posterior information of genotype clusters from a clustering algorithm;
assigning each sample into genotype clusters according to a cluster expectation or likelihood, appropriate for the model;
calculating genotype cluster center locations by maximizing likelihood; and
selecting the model with a greatest maximum likelihood.

15. The method according to claim 1 further comprising:
using the created probeset to genotype said SNP.

16. The method according to claim 1, wherein clustering the sample data comprises iteratively assigning, until a determined threshold of convergence is reached, the sample data into homozygous genotype clusters based on an absolute contrast threshold, heterozygous genotype clusters based on a low contrast threshold, and determined OTV genotype clusters by identifying sample data outside of the homozygous genotype clusters and heterozygous genotype clusters.

17. The method according to claim 16, wherein iteratively updating genotyping call assignments to converged clusters and cluster centers comprises, upon reaching the determined threshold of convergence, calling at least one of a homozygous genotype cluster, heterozygous genotype cluster, and OTV genotype cluster based on the clustered sample data.

* * * * *